(12) United States Patent
Liu et al.

(10) Patent No.: US 8,859,828 B2
(45) Date of Patent: Oct. 14, 2014

(54) CONVERSION OF SUGAR, SUGAR ALCOHOL, OR GLYCEROL TO VALUABLE CHEMICALS USING A PROMOTED ZIRCONIUM OXIDE SUPPORTED CATALYST

(75) Inventors: Aiguo Liu, Louisville, KY (US); Wayne Turbeville, Crestwood, KY (US); Christopher C. Luckett, Louisville, KY (US); Hui Hui (Faye) Li, Baltimore, MD (US)

(73) Assignee: Clariant Corporation, Louisville, KY (US)

( * ) Notice: Subject to any disclaimer, the term of this patent is extended or adjusted under 35 U.S.C. 154(b) by 559 days.

(21) Appl. No.: 13/254,264

(22) PCT Filed: Mar. 3, 2010

(86) PCT No.: PCT/US2010/000651
§ 371 (c)(1),
(2), (4) Date: Sep. 1, 2011

(87) PCT Pub. No.: WO2010/101637
PCT Pub. Date: Sep. 10, 2010

(65) Prior Publication Data
US 2011/0319672 A1 Dec. 29, 2011

Related U.S. Application Data

(60) Provisional application No. 61/156,859, filed on Mar. 2, 2009.

(51) Int. Cl.
| | |
|---|---|
| C07C 27/04 | (2006.01) |
| B01J 37/03 | (2006.01) |
| B01J 23/28 | (2006.01) |
| B01J 23/86 | (2006.01) |
| B01J 23/26 | (2006.01) |
| B01J 35/10 | (2006.01) |
| C07C 29/00 | (2006.01) |
| B01J 35/00 | (2006.01) |
| B01J 23/30 | (2006.01) |
| B01J 37/00 | (2006.01) |
| B01J 21/06 | (2006.01) |

(52) U.S. Cl.
CPC .............. *B01J 21/066* (2013.01); *B01J 37/031* (2013.01); *B01J 23/28* (2013.01); *B01J 23/866* (2013.01); *B01J 23/26* (2013.01); *B01J 35/1019* (2013.01); *B01J 35/1014* (2013.01); *C07C 29/00* (2013.01); *B01J 35/002* (2013.01); *B01J 23/30* (2013.01); *B01J 37/0009* (2013.01); *B01J 23/868* (2013.01)
USPC ............ 568/903; 568/861; 568/863; 568/881

(58) Field of Classification Search
CPC .... C07C 29/60; C07C 29/141; C07C 29/172; C07C 31/26
USPC .................. 568/861, 863, 881, 903
See application file for complete search history.

(56) References Cited

U.S. PATENT DOCUMENTS

| | | |
|---|---|---|
| 4,233,139 A | 11/1980 | Murrell |
| 5,391,362 A | 2/1995 | Reinalda et al. |
| 6,034,029 A | 3/2000 | Wulff-Doring et al. |
| 6,291,725 B1 | 9/2001 | Chopade |
| 6,479,713 B1 | 11/2002 | Werpy et al. |
| 6,900,361 B2 | 5/2005 | Elliott |
| 6,982,328 B2 | 1/2006 | Werpy |
| 7,384,987 B2 | 6/2008 | Iordache-Cazana |
| 2004/0179994 A1* | 9/2004 | Fenouil et al. ............... 423/608 |
| 2004/0259731 A1* | 12/2004 | Yan ............................. 502/439 |
| 2007/0036710 A1 | 2/2007 | Fenouil |
| 2007/0191212 A1 | 8/2007 | Schubert |
| 2009/0012334 A1 | 1/2009 | Hulteberg |
| 2009/0305882 A1 | 12/2009 | Dahar |

* cited by examiner

*Primary Examiner* — Sudhakar Katakam

(57) ABSTRACT

A process for converting a sugar, sugar alcohol, or glycerol to a valuable chemical is described. The process may use a support comprising zirconium oxide promoted by a polyacid or promoter material. A catalytically active metal may be impregnated on the polyacid-promoted zirconium oxide support and the catalyst may then be introduced the sugar, sugar alcohol, or glycerol a source of hydrogen under reaction conditions. At least 40 wt % of the sugar, sugar alcohol or glycerol may be converted to a polyol and/or a shorter carbon-chain alcohol that may include at least one of propylene glycol, ethylene glycol, glycerin, methanol, ethanol, propanol and butandiols. Specific processes for converting glycerin having a selectivity for propylene glycol and for converting sorbitol with a selectivity for propylene glycol, ethylene glycol, and/or glycerin are also described.

27 Claims, No Drawings

CONVERSION OF SUGAR, SUGAR ALCOHOL, OR GLYCEROL TO VALUABLE CHEMICALS USING A PROMOTED ZIRCONIUM OXIDE SUPPORTED CATALYST

CROSS REFERENCE TO RELATED APPLICATION

This application claims the benefit of U.S. Provisional Application No. 61/156,859, filed on Mar. 2, 2009, the contents of which are incorporated by reference herein. This application is related to International Patent Application PCT/US2010/00651, filed Mar. 3, 2010.

TECHNICAL FIELD

This application includes embodiments and claims pertaining to a process for converting polyols such as sugar, sugar alcohols, or glycerol into commercially-valuable, products and intermediates for further use in industrial and/or end-user applications. The sugars, sugar alcohol or glycerol may be obtained from a biomass source, but need not be so obtained. The conversion of these materials may include the use of catalyst with a zirconium oxide support or carrier, including a support promoted by the incorporation of a poly-acid or other promoter material.

BACKGROUND ART

Physical and chemical stability is a major concern in the application of heterogeneous catalysts in aqueous phase reactions. Traditional $SiO_2$ or $Al_2O_3$ based catalyst supports are prone to prone to disintegration or attack when used in an aqueous solution, which usually results in loss of mechanical strength of the catalyst body that is targeted for a long-term industrial application. In laboratory and industrial applications, the mechanical strength of heterogeneous catalysts is generally evaluated by crush strength, wherein increasing crush strength values are generally indicative of improved mechanical strength of the support or carrier.

Catalytic supports or carriers may comprise a variety of materials, such as zirconium oxide, also referred to as zirconia, which is a known high temperature refractory material with extensive industrial applications. It is also a known catalyst support material because of its high physical and chemical stability and moderate acidic surface properties. Nonetheless, the use of zirconia as a supporting material for heterogenous catalysts has limited application due to its relatively high cost and difficulties in forming certain shapes from this material. Furthermore, the zirconia often undergoes a phase transformation that results in a substantial change in structure, and loss of surface area and pore volume. This reduces the strength and durability of the zirconia. To inhibit phase transformation effects, stabilizing agents are used to maintain preferable phases.

One non-exhaustive example of technology directed to making zirconia catalyst supports is described in WO 2007/092367 (filed by Saint-Gobain), which describes a formed ceramic body comprising tetragonal zirconia as the primary phase with a surface area greater than 75 $m^2/g$ and a pore volume of over 0.30 mL/g. In one aspect of the invention, a process for making a zirconia carrier is described and is further defined by the use of inorganic or organic binder(s) and/or stabilizing agents. The stabilizing agents may be selected from among silicon oxide, yttrium oxide, lanthanum oxide, tungsten oxide, magnesium oxide, calcium oxide and cerium oxide.

A recent trend is to use plant or animal-derived compounds (e.g. biomass) as the feedstock to make valuable chemicals that are typically derived from petroleum. One example is the use of glycerin (glycerol) to make propylene glycol (PG), which is extensively used in many applications such as the production of polyester, polyurethane polymers and as antifreeze and de-icing compounds, and therefore remains a useful chemical. Other examples of commercially important intermediate chemicals that can be derived from biomass and subsequently converted to high value chemicals include use of sugars or sugar alcohols (e.g. glucose or sorbitol) to make shorter-carbon chain sugar alcohols through hydrogenation and hydrogenolysis. In both processes, hydrogen is added to the target compound in the presence of a catalyst and under aqueous conditions. Hydrogenolysis is a process that involves the breakage of chemical bonds, such as a carbon-carbon or carbon-oxygen bonds, through addition of hydrogen.

One non-exhaustive example of a catalytic hydrogenation process is described in U.S. Pat. No. 6,982,328 (Werpy et al.). Werpy et al. discloses an invention that includes a process of forming glycerol, ethylene glycol, lactic acid and propylene glycol from plant matter by adding water, heating and filtering the plant matter. In one aspect of the invention, a reduction step (400) can comprise catalytic hydrogenation, exposing saccharides to a catalyst comprising a support and one or more members of the groups consisting of Ru (ruthenium), Ni (nickel), Pt (platinum) and Pd (palladium). The catalyst support can comprise carbon and/or other insoluble support material, such as titania and zirconia.

An additional non-exhaustive example of related technology is described in U.S. Pat. No. 6,900,361 (Elliott et al.). Elliott et al. discloses an invention that includes a process for converting lactose into polyols that includes a hydrogenation step that involves heating the hydrolyzate in the presence of hydrogen and a catalyst. The hydrogenation catalyst may be any type of catalyst capable of initiating and sustaining hydrogenation of a monosaccharide. Such catalysts are well known and typically are metal catalysts such as Ru (ruthenium), Ni (nickel), Co (cobalt), Cu (copper) and alloys thereof. The metal catalysts may be provided on various support substrates such as titania, zirconia, alumnia, silica, alumina/silica and carbon. According to certain embodiments, the catalyst support is especially stable in aqueous medium or phase chemical reaction conditions. According to Elliot et al., exemplary stable supports include titania in the rutile form, zirconia in the monoclinic form, high-surface area granulated carbons, or boehmite.

It has now been found that zirconia promoted with a poly-acid or similarly functioning promoter material yields a zirconia-based support or catalyst with improved physical properties for extrusion and/or use as a carrier or support for a catalyst in industrial applications performed in an aqueous environment, including the conversion of sugars, sugar alcohols or glycerol into polyols and/or shorter-carbon chain chemicals and materials for use in other applications. The improvement to mechanical strength of the catalyst support or carrier inhibits metal leaching into an aqueous solution, improving the mechanical strength and stability of the support or carrier in such conversion reaction processes.

Certain embodiments of the invention represent improvements in supports or carriers utilized in catalysts and as employed in conversion reactions in which a catalyst is deployed.

DISCLOSURE OF EMBODIMENTS OF THE INVENTION

A process for converting a sugar, sugar alcohol or glycerol to a polyol and/or an alcohol comprising a shorter carbon-chain backbone is described in various embodiments. The process may comprise selecting a support comprising zirconium oxide promoted by a polyacid or promoter material and impregnating the polyacid-promoted zirconium oxide support with one or more catalytically active metals and optionally, one or more promoters. The polyacid-promoted zirconium oxide supported catalyst may then be introduced to the sugar, sugar alcohol or glycerol under reaction conditions and with a source of hydrogen. At least 40 wt. % of the sugar, sugar alcohol or glycerol may be converted to a polyol and/or a shorter carbon-chain alcohol that may include at least one of propylene glycol (1,2-propanediol), ethylene glycol, trimethylene glycol (1,3-propanediol), glycerin, methanol, ethanol, propanol and butandiols.

In other embodiments, a process for converting glycerin having a selectivity for propylene glycol and a process for converting sorbitol with a selectivity for propylene glycol, ethylene glycol, and/or glycerin are further described.

In some embodiments, the polyacid-promoted zirconium oxide support has a molar ratio of zirconium to promoter in the range between 2:1 and 20:1. In other embodiments, the support comprises zirconium and chromium and has a molar ratio of zirconium to chromium in the range between 4:1 and 16:1.

MODES FOR CARRYING OUT EMBODIMENTS OF THE INVENTION

In one embodiment of the invention, a process for converting one or more sugars, sugar alcohols or glycerol to a polyol or an alcohol comprising a shorter carbon-chain backbone is described. As used herein, unless otherwise qualified, the term polyol(s) refers to any polyhydric alcohol containing more than one hydroxyl group. As broadly defined, polyol may encompass both the reactants and/or the products described above. The resulting polyol or shorter-carbon chain alcohol may include at least one of propylene glycol (1,2-propanediol), ethylene glycol, trimethylene glycol (1,3-propanediol), glycerin, methanol, ethanol, propanol and butandiols.

The process may include selecting a support comprising zirconium oxide promoted by a polyacid/promoter material and impregnating the support with a catalytically active metal catalyst. A sugar, sugar alcohol or glycerol is passed over the zirconium oxide supported catalyst with hydrogen under suitable reaction conditions that may include an aqueous phase environment. Preferably at least 40% of the sugar, sugar alcohol or glycerol is converted to a commercially important polyol or shorter-carbon chain alcohol.

The catalytically active metal catalyst may be selected from the group consisting of Group 4 (Group IVA), Group 10 (Group VIII) and Group 11 (Group IB) metals, and combinations thereof. These metals include, but are not limited to, copper, nickel, tin, ruthenium, rhenium, platinum, palladium, cobalt, iron and combinations thereof. The catalytically active metals may be deposited on the catalyst support using any of the standard, well-known techniques, including, but not limited to, impregnation, ion-exchange, precipitation, grafting, and the like.

In one embodiment, a copper catalyst may be used with the polyacid-promoted zirconium oxide catalyst support for the process for converting glycerol (also referred to as "glycerin") to propylene glycol. In this embodiment, a target load of copper catalyst on the support may comprise a range between of 5 wt. % and 30 wt. %. The target load of copper may further comprise a range of 10 wt. % to 20 wt. %. The target load of copper may be further characterized as approaching approximately 10%. The conversion rate of glycerin to propylene glycol may be at least 40 wt. % and a may have a selectivity to propylene glycol of at least 75 molar %.

In another embodiment of the process for converting glycerol to propylene glycol, the target load of copper on the support may be approximately 15 wt. %. The conversion rate of glycerol to propylene glycol may be at least 65% and may have a selectivity of propylene glycol of at least 85 molar %.

In a further embodiment, a process for converting sorbitol with a selectivity for propylene glycol, ethylene glycol, and/or glycerin at reaction conditions is described. In this embodiment, a nickel and tin catalyst may be used with the polyacid-promoted zirconium oxide catalyst support. The target load of nickel on the support may be approximately 10 wt. % to about 30 wt. % and the target load of tin on the support may be about 200 ppm to 5000 ppm.

In an embodiment with a target load of tin on the support approaching approximately 300 ppm, the process may further comprise a conversion rate of sorbitol of at least 65% and a selectivity for propylene glycol in a range between 35 molar % and 45 molar %, a selectively for ethylene glycol in a range between 10 molar % and 20 molar %, and a selectively for glycerin in a range between 15 molar % and 25 molar %.

In an embodiment with a target load of tin on the support approaching approximately 700 ppm, the process may further comprise a conversion rate of sorbitol of at least 70% and a selectivity for propylene glycol in a range between 25 molar % and 35 molar %, a selectivity for ethylene glycol in a range between 10 molar % and 20 molar %, and a selectivity for glycerin in a range between 15 molar % and 25 molar %.

In some embodiments, the catalyst support may comprise a zirconium compound and a polyacid/promoter material wherein the mixture may have a molar ratio between about 2:1 and 20:1. Alternatively, the molar ratio of zirconium to polyacid/promoter material (Zr:Promoter) may be in a range between 4:1 and 16:1; or between 8:1 and 16:1; or between about 10:1 and 14:1; or about 13:1; or about 12:1; or about 8:1. In other embodiments, the catalyst support may be made from any material that is capable of withstanding an aqueous phase environment for a sufficiently long operating period under elevated temperature and pressure conditions.

In various embodiments, a polyacid-promoted, zirconium oxide supported catalyst may be contacted with the compound to be converted in the presence of hydrogen at elevated temperatures and pressures.

The compound to be converted may be selected from the group consisting of a sugar, a sugar alcohol, sorbitol, glycerin, glycols, triols, polyglycols, and combinations thereof. The sugars may be selected from carbohydrates with six carbon chains, such as, without limitation, glucose, galactose, maltose, lactose, sucrose, allose, altrose, mannose, gulose, idose, talose, or carbohydrates with five-carbon chains, such as, without limitation, ribose, arabinose, xylose, lyxose. These compounds may be obtained from a biomass source, but need not be so obtained.

The compounds to be converted may be mixed with a polar liquid, such as, without limitation, water, methanol, ethanol, ethylene glycol, propylene glycol, n-propanol, i-propanol and combinations thereof, to form a carbohydrate solution. Preferably, the carbohydrate comprises from about 15 wt % to about 50 wt % of the carbohydrate solution, and more preferably from about 20 wt % to about 35 wt %.

In an exemplary embodiment, without limitation, the polyacid-promoted, zirconium oxide supported catalyst may be placed in a fixed bed of a reactor, then continuously feeding an aqueous solution of compound to be converted through the catalyst bed at a predetermined feed rate, while maintaining the catalyst bed at a temperature from about 180° C. to about 250° C. and maintaining a partial pressure of hydrogen at 100 bar to 160 bar.

In another embodiment, the catalyst bed is heated to a temperature of from about 180° C. to about 250° C., the hydrogen gas is introduced to the reactor until the reactor has a pressure of from about 100 bar to about 160 bar, the liquid feed stream comprises about 20 wt % to about 35 wt % glycerin in water which is fed into the reactor at an LHSV of from about 0.5 to about 6.0. The reaction pH is controlled by addition of base as necessary to maintain the pH between 9.0 and 12.0, and preferably at about 11.0.

In yet another embodiment, the catalyst bed may be heated to a temperature from about 180° C. to about 300° C. Hydrogen gas may then be introduced to the reactor until the reactor has a pressure of from about 70 bar to about 210 bar. A liquid feed stream comprising about 15 wt % to about 50 wt % of the compound to be converted in water may then be fed into the reactor at a liquid hourly space velocity (LHSV) of about 0.2 to about 6.0.

Certain embodiments of the invention include the product and process of making a catalyst or catalyst support/carrier comprising zirconium oxide ($ZrO_2$) promoted by a polyacid or a functionally-similar, promoter material, generally referred to as the "polyacid/promoter material." The polyacid/promoter material may comprise materials from the Group 6 (Group VIA) metals including chromium (Cr), molybdenum (Mo), and tungsten (W), as well as phosphorous acids, sulfuric acid, acetic acid, citric acid and other polyorganic acids. As used herein, unless otherwise qualified, the term polyacid(s) refers to a chemical or composition having more than one multi-donor proton in acid form. The finished catalyst or catalyst support/carrier may have a molar ratio of zirconium to promoter (Zr:Promoter) between 2:1 and 20:1.

In another embodiment, a method of preparing a catalyst or catalyst support comprising, or alternatively, consisting essentially of, a zirconium compound and a promoter includes mixing a polyacid/promoter material selected from the group consisting of a polyacid, a polyacid comprising the oxide or acid form of chromium (Cr), molybdenum (Mo), tungsten (W), and combinations thereof with a zirconium compound. The zirconium compound and the polyacid/promoter material may be co-precipitated by mixing an aqueous basic solution to form a zirconium-promoter precursor. Alternatively, the zirconium compound may be precipitated first and then the polyacid/promoter material may be mixed with the precipitated zirconium to form the zirconium-promoter precursor. The zirconium-promoter precursor can then be dried, shaped and calcined in accordance with well-known processes to form a finished catalyst or catalyst support. The finished catalyst or catalyst support may have a molar ratio of Zr:Promoter between 2:1 and 20:1.

Other embodiments of the invention are directed to the use of the catalyst support and at least one catalytically active metal to form a catalyst for the conversion of sugars, sugar alcohols or glycerol into commercially-valuable chemical products and intermediates, including, but not limited to, polyols or an alcohol comprising a shorter carbon-chain backbone such as propylene glycol (1,2-propanediol), ethylene glycol (1,2-ethanediol), glycerin, trimethylene glycol (1,3-propanediol), methanol, ethanol, propanol and butandiols. As used herein, unless otherwise qualified, the term polyol(s) refers to any polyhydric alcohol containing more than one hydroxyl group. As broadly defined, polyol may encompass both the reactants and/or the products described above.

The zirconium may be selected from the group consisting of zirconium or zirconyl halides, zirconium or zirconyl nitrates, or zirconyl organic acids, and combinations thereof. The zirconium compounds may comprise a variety of materials, including zirconium and zirconyl in salt forms of halides such as $ZrCl_4$ or $ZrOCl_2$; nitrates such as $Zr(NO_3)_2 \cdot 5H_2O$ or $ZrO(NO_3)_2$, and organic acids such as $ZrO(CH_3COO)_2$. Other zirconium compounds are envisioned and not limited to those specifically identified herein. In solution, zirconium can be in a form of zirconyl ($ZrO^{2+}$) or zirconium ion ($Zr^{4+}$ or $Zr^{2+}$) that may be obtained by dissolving corresponding salts in water.

The polyacid/promoter material may be the Group 6 metals comprising chromium (Cr), tungsten (W), and molybdenum (Mo) in oxide or acid form(s) that form a polyacid after being dissolved in a water solution. In one embodiment, the polyacid may be selected from the group consisting of $CrO_3$, $Cr_2O_3$, and combinations thereof. In another preferred embodiment, the polyacid/promoter material is $Cr^{6+}$ or Cr(VI), as may be found in $CrO_3$. In yet other embodiments, the polyacid/promoter material may be selected from the group consisting of phosphoric acid, sulfuric acid, acetic acid, citric acid and combinations thereof.

One embodiment for preparing a catalyst or catalyst support/carrier characterized by having a zirconium oxide ($ZrO_2$) base involves preparing a zirconium compound and a polyacid/promoter material and then mixing these compounds in acidic conditions having a pH ranging from about 0.01 to about 4. A base solution may be introduced for promoting precipitation of the desired precipitate. The base solution may include aqueous ammonia, aqueous sodium hydroxide, or other aqueous basic solutions for adjusting the pH conditions to yield a zirconium salt precipitate. In another embodiment, the polyacid/promoter material is initially dissolved in a base solution, such as ammonia hydroxide, followed by mixing with the zirconium compound.

In various embodiments, the initial molar ratio of the zirconium to the polyacid/promoter material (Zr:Promoter) may fall in a range between 2:1 and 20:1; and alternatively between 4:1 and 16:1; or between 8:1 and 16:1; or about 12:1; or about 8:1. The final molar ratio of the zirconium and promoter may fall in a range of 2:1 to 20:1; and alternatively between 4:1 and 16:1; or between 8:1 and 16:1; or between about 10:1 and 14:1; or about 13:1; or about 12:1; or about 8:1. In one embodiment, a molar ratio of zirconium to chromium (Zr:Cr) may fall in a range between 4:1 and 16:1; and alternatively between 8:1 and 16:1, or between 10:1 and 14:1; or about 13:1; or about 12:1; or about 8:1.

In various embodiments, zirconyl nitrate ($ZrO(NO_3)_2$) and chromium oxide ($CrO_3$ (Cr VI) or $Cr_2O_3$ (Cr III) (polyacid/promoter material) serve as the respective starting materials for preparation of a catalyst or catalyst support/carrier. The initial molar ratio of the zirconium base metal and chromium polyacid/promoter material (Zr:Cr) may be in the range between 2:1 and 20:1, or alternatively between 4:1 and 12:1, or between 8:1 and 12:1 or between 6:1 and 10:1. The starting materials may be mixed under acidic conditions (e.g., a pH value approximately 0.01 to 1) to prevent hydrolyzing the catalyst and then pumped into a vessel or reactor and mixed with aqueous ammonia (15% $NH_3$) and stirred. The aqueous ammonia possesses a pH value of approximately 12.5. After mixing of the Zr/Cr solution with the aqueous ammonia, the pH value is within a range of 7.5 to 9.5. Optionally, if the pH value is beyond the range of 7.5 to 9.5, adjustments may be performed with the addition of the appropriate acidic or basic material(s) or solution(s) to bring the pH value within the range.

After mixing of the starting materials, the zirconium-promoter precipitate may be filtered and separated from the liquid, yielding a filtrate-cake. If filtered, a variety of methods and/or apparatuses may be utilized, including the use of filter paper and vacuum pump, as well as centrifugal separation, other vacuum mechanisms and/or positive pressure arrangements. In one embodiment, the drying of the filtrate-cake may be achieved by dividing (e.g., breaking) the filtrate-cake into smaller quantities to facilitate air drying at ambient conditions. The division (e.g. breaking) of the filtrate-cake may be manual or automated. Optionally, the filtrate-cake may be washed if any of the feed materials used in the process contain undesirable elements or compounds, such as chloride or sodium. Typically, one (1) to ten (10) washings, or even more washings may be required if undesired elements or other contaminants are present in the feed materials.

The precipitated zirconium-promoter precursor (in the form of a filtrate cake) may be dried at ambient conditions (e.g. room temperature and ambient pressure) or under moderate temperatures ranging up to about 120° C. In one embodiment, the zirconium-promoter precursor is dried at a temperature ranging between 40° C. and 90° C. for about 20 minutes to 20 hours, depending on the drying equipment used. In other embodiments, a heated mixer may be used to mix the zirconium precipitate with the polyacid/promoter material thereby allowing drying time to be reduced to less than 1 hour. In one embodiment, the zirconium-promoter precursor or only the precipitated zirconium is dried until a loss of ignition ("LOI") is achieved in a range between about 60 wt. % to about 70 wt. %. As used herein, LOI may be understood as the weight loss percentage by ignition of the material at approximately 480° C. for approximately two (2) hours. In other embodiments, the zirconium-promoter precursor or the precipitated zirconium is dried until a LOI of about 64 wt. % to 68 wt. % is achieved, and more preferably, about 65 wt. % to 68 wt. %.

In the various embodiments, the zirconium-promoter precursor may be dried to achieve a mixture that is suitable for extrusion without any binder(s), extrusion aid(s), or stabilizing agent(s). In other words, the zirconium-promoter precursor is dried to be capable of forming a shape suitable for a finished catalyst or catalyst support/carrier in the absence of any stabilizing agent, binder or extrusion aid. The following compounds have been described in the prior art as a stabilizing agent, binder, or extrusion aid, and all of these compounds are absent in one or more embodiments described in this application: silicon oxide, yttrium oxide, lanthanum oxide, tungsten oxide, magnesium oxide, calcium oxide, cerium oxide, other silicon compounds, silica-alumina compounds, graphite, mineral oil, talc, stearic acid, stearates, starch, or other well-known stabilizing agent, binder or extrusion aid.

Forming of the dried zirconium-promoter precursor into any shape suitable for a finished catalyst or catalyst support/carrier maybe done by any of forming processes that are well known in the art. In a preferred embodiment, the dried zirconium-promoter precursor is extruded. A screw extruder, press extruder, or other extrusion devices and/or methods known in the art may be used. Alternatively, the dried zirconium-promoter precursor may be pressed such as by tabletting, pelleting, granulating, or even spray dried provided the wetness of the dried zirconium-promoter precursor is adjusted for the spray-drying material, as is well-known in the art. Optionally, the extruded zirconium-promoter precursor may be dried at moderate temperatures (e.g., up to about 120° C.) for a moderate period of time (e.g., typically about 1 to 5 hours) after being formed.

The extruded or other shaped catalyst or catalyst support/carrier may be calcined at temperatures ranging from about 300° C. to 1000° C. for approximately 2 to 12 hours, and preferably from about 400° C. to 700° C. for approximately 3 to 5 hours. In one embodiment, an extruded chromium-promoted zirconium oxide precursor is calcined at about 600° C. for approximately three hours. Alternatively, an extruded chromium promoted zirconium oxide precursor may be calcined at a ramp of 1 degree per minute (abbreviated as "deg/m" or "° C./m" or "°/min") to 600° C. and dwell for approximately 3 hours. In another embodiment, an extruded polyacid-promoted zirconium precursor is calcined at about 300° C. to 1000° C., or at about 400° C. to 700° C., or at about 500° C. to 600° C. for approximately 2 to 12 hours.

Using the various method embodiments described above, the finished product is a polyacid-promoted zirconium oxide catalyst or catalyst support/carrier having a crystalline structure of one or more of the monoclinic, tetragonal, cubic and/or amorphous phases as determined by well-known powder x-ray diffraction (XRD) techniques and devices. For example, see "Introduction to X-ray Powder Diffraction," R. Jenkins and R. L Snyder, Chemical Analysis, Vol. 138, John Wiley. & Sons, New York, 1996. Typically, the tetragonal phase of zirconium oxide may be determined by measuring the intensity of a sample at a d-spacing of 2.97 angstroms (Å), while the monoclinic phase is measure at a d-spacing of 3.13 angstroms (Å). In other embodiments, the finished catalyst or catalyst support/carrier may be further characterized as comprising about 50 wt. % to 100 wt. % tetragonal phase of zirconium oxide as its crystalline structure. In another embodiment, the finished catalyst or catalyst support may be further characterized as comprising 0 to 50 wt. % monoclinic phase of zirconium oxide. Alternatively, the crystalline structure may comprise above 80 wt. % tetragonal phase of zirconium oxide, or about 85 wt. % tetragonal phase of zirconium oxide.

For a catalyst or catalyst support/carrier comprising a Zr/Cr composition, the more chromium used in the process, the more tetragonal phase crystalline structure is achieved as product. For example, a 4:1 molar ratio yields almost 100% tetragonal phase of zirconium oxide. An 8:1 molar ratio yields almost 100% tetragonal phase of zirconium oxide. At a 12:1 molar ratio, the crystalline structure is approximately 85 wt. % to 90 wt. % tetragonal phase and approximately 15 wt. % to 10 wt. % monoclinic phase of zirconium oxide.

The polyacid-promoted zirconium oxide catalyst or catalyst support/carrier as described above may have a crush strength in a range between 67 N/cm (1.5 lb/mm) and 178 N/cm (4.0 lb/mm.) Alternatively, the catalyst or catalyst support has a minimum crush strength of at least 45 N/cm (1 lb/mm) or at least 90 N/cm (2 lb/mm), depending on its use. The crush strength of a catalyst or catalyst support/carrier may be measured using ASTM D6175-03 (2008), Standard Test Method for Radial Crush Strength of Extruded Catalyst and Catalyst Carrier Particles.

In other embodiments, the finished polyacid-promoted zirconium oxide catalyst or catalyst support/carrier may have a surface area as measured by the BET method in a range between 20 $m^2/g$ and 150 $m^2/g$. Alternatively, the finished zirconium oxide catalyst or catalyst support/carrier may have a surface area in a range between 80 $m^2/g$ and 150 $m^2/g$, and preferably about 120 $m^2/g$ and 150 $m^2/g$.

The polyacid-promoted zirconium oxide catalyst or catalyst support/carrier may also have a pore volume in a range between 0.10 cc/g and 0.40 cc/g. Generally, for initial molar ratios between 4:1 and 16:1, the pore volume consistently yields values in a range between 0.15 cc/g and 0.35 cc/g. For initial molar ratios approximately 8:1, the pore volume consistently yields values in a range between 0.18 cc/g and 0.35 cc/g.

Industrial Applicability

The polyacid-promoted zirconium oxide support/carrier may be combined with one or more catalytically active metals to form a catalyst for use in many industrial processes, including aqueous phase reactions under elevated temperature and pressure conditions. In one embodiment, an extruded chromium-promoted zirconium oxide support exhibits high hydrothermal stability and provides a durable support/carrier for aqueous phase hydrogenation or hydrogenoloysis reactions. These reactions include the conversion of glycerol and sorbitol to various polyols or shorter-carbon chain alcohols that may include, but are not limited to, at least one of propylene glycol, ethylene glycol, trimethylene glycol, glycerin, methanol, ethanol, propanol and butandiols. n other embodiments, a polyacid-promoted zirconia support maybe used as a catalyst or catalyst support/carrier in other industrial processes, including aqueous, hydrocarbon and mixed phases.

EXAMPLES

The following examples are for illustrative purposes disclosing multiple embodiments of the invention, and are not a limitation on the embodiments and/or the claims presented herein. Unless otherwise designated, chemicals or materials designated by a percentage refer to weight percentage (wt. %) of the chemical or material. As used herein "selectivity" or "molar selectivity" is defined as the percentage of carbon in a particular product over the total consumed carbon in the feed.

Example 1

Chromium (VI) Promoter

A first solution (Solution 1) was prepared using 10 g of $CrO_3$ dissolved in 10 mL of de-ionized water (hereinafter referred to as "DI-H2O"). Solution 1 was then mixed with 500 g of zirconium nitrate solution (20% $ZrO_2$). A second solution (Solution 2) was prepared using 400 mL DI-$H_2O$ and 250 mL of ammonia hydroxide solution (30%). Solution 1 was transferred into Solution 2 drop-wise with concurrent stirring. The pH of the mixed solutions (Sol. 1 and Sol. 2) dropped from approximately 12 to approximately 8.5.

Precipitation occurred due to a decrease in the pH value. The precipitate was left in the mother liquor to age for approximately one hour. Similar to Examples 2 and 3 described below, the precipitate is processed in a relatively consistent manner. The generated precipitate was filtered without washing. The filter cake was manually divided into smaller portions and left to dry under ambient temperature for approximately four days to reach an LOI in a range between about 65 wt. % and 68 wt. %. The dried filter cake was then ground and extruded with a ⅛" die yielding a ⅛" extrudate material. The extrudate was additionally dried at approximately 120° C. for approximately 3 hours. Thereafter, the extrudate was calcined at a ramp of 1 deg/m to 600° C. for approximately 3 hours.

The obtained extrudate had a surface area of approximately 63 $m^2/g$, a pore volume of approximately 0.22 cc/g and a crush strength value of approximately 134 N/cm (3.02 lb/mm.) The calcined extrudate material was generally comprised of a mixture of tetragonal phase and monoclinic phase $ZrO_2$ as interpreted and indicated by the XRD data.

Example 2

Chromium (VI) Promoter—$NH_4OH$ (Aqueous Basic Solution)

300 mL of concentrated $NH_4OH$ (28-30%) was diluted with 500 mL DI-H2O and loaded into a 2000 mL tank reactor. The reactor was then preheated to 35° C. A solution of 500 g zirconium nitrate solution (20% wt $ZrO_2$) was preheated to 35° C. and pumped into the reactor tank in a one hour period under vigorous stirring. The pH of the solution decreased from a value of about 12.5 to approximately 8.5. After aging for an hour under slower stirring, the precipitate was filtered. The obtained filter cake was then mixed with 10 g $CrO_3$ by mechanical stirring for about an hour. The obtained mixture was dried under vacuum at 35° C. to 40° C. until LOI reached a range and about 65 wt. % to about 70 wt. %. The dried powder was then extruded and calcined under a temperature program of ramp at 5° C./min to 110° C., hold (dwell) for 12 hours, ramp at 5° C./min to 600° C. and hold for 6 hours. Typical properties of the obtained extrudates include a crush strength of 137 N/cm (3.08 lb/mm), a pore volume of 0.21 cc/g, and a surface area of 46 $m^2/g$. XRD analysis showed a mixture of tetragonal phase (d=2.97 Å) and monoclinic phase of $ZrO_2$ (d=3.13 Å).

Example 3

Chromium (VI) Promoter—NaOH (Aqueous Basic Solution)

NaOH instead of $NH_4OH$ was used for this preparation. A total of 500 mL of 25% wt NaOH solution was preheated to 35° C. 200 mL of the NaOH solution and 1200 mL DI-$H_2O$ was loaded into a 2000 mL tank reactor. A solution of 500 g zirconyl nitrate solution (20% wt $ZrO_2$) was preheated to 35° C. and pumped into the tank reactor in a one hour period under vigorous stirring. The 25% NaOH solution was added as necessary when pH dropped below 8.5 during the precipitation. After aging for an hour under slower stirring, the precipitate was filtered. The filter cake was re-slurred with DI-$H_2O$ in 1:1 volumetric ratio and stirred for 15 min before filtration. The same procedure was repeated until conductivity of the filtrate was below 200 μS, which usually required washing the filter cake about 4 to 8 times. The washed filter cake was then mixed with 10 g $CrO_3$ and dried at 70° C. until 64 wt. % to 70 wt. % LOI was achieved. A similar procedure as described in Example 2 was followed for extrusion and calcinations of the filter cake. Typical properties of the obtained extrudates include a crush strength of 94 N/cm (2.12 lb/mm), a pore volume of 0.23 cc/g, and a surface area of 94 $m^2/g$. XRD analysis showed a mixture of tetragonal phase (d=2.97 Å) and monoclinic phase of $ZrO_2$ (d=3.13 Å).

Example 4

Chromium (III) Nitrate Promoter 55 g of chromium (III) nitrate solution (9.6% wt Cr) was mixed with 500 g zirconyl nitrate solution (20% wt $ZrO_2$). Similar precipitation and washing procedure as example 2 were applied. After washing, similar drying, extrusion and calcination procedures as described in Example 3 were applied. Typical properties of the obtained extrudates include a crush strength of 111 N/cm (2.49 lb/mm), a pore volume of 0.33 cc/g, and a surface area of 136 $m^2/g$. XRD analysis showed a mixture of tetragonal phase (d=2.97 Å) and monoclinic phase of $ZrO_2$ (d=3.13 Å).

Example 5

Phosphorous Promoter 125 g of zirconyl nitrate solution (having about 20% Zr as $ZrO_2$) was diluted by the addition of DI-$H_2O$ to a total mass of 400 g. Thereafter, 12 g of 85% $H_3PO_4$ was added drop-wise to the diluted zirconyl nitrate solution with concurrent stirring to yield an initial molar ratio of Zr/P equal to 2:1. A gel formation was observed. The mixed solution was continuously stirred for another 30 minutes at ambient temperature. $NH_3H_2O$ was added drop-wise afterward until a total gel formation with a pH having a value in the range of 6.5 to 7.5 was produced.

An additional quantity of DI-$H_2O$ was added, approximately 100 mL, with continuous stirring for approximately 12 hours under ambient temperature to disperse the gel formation. The generated precipitate was filtered without washing. The filter cake was manually divided into smaller portions and left to dry in the air under ambient temperature for approximately four days. The dried filter cake was then ground and extruded. The extrudate was additionally dried at approximately 120° C. for approximately 3 hours. Thereafter, the extrudate was calcined at a ramp of 1 deg/m to 600° C. for approximately 3 hours.

The obtained extrudate material had a surface area of approximately 19 $m^2/g$, a pore volume of approximately 0.19 cc/g and a crush strength value of approximately 85 N/cm (1.9 lb/mm.) The calcined extrudate material was generally comprised of amorphous phase $ZrO_2$ as interpreted and indicated by the XRD data.

Example 6

Phosphorous Promoter

The procedure as provided in Example 5 above was utilized, except that 250 g of zirconyl nitrate solution was used in order to obtain an initial molar ratio of Zr/P of approximately 4:1. The obtained extrudate had a surface area of approximately 20.9 $m^2/g$, a pore volume of approximately 0.19 cc/g and a crush strength value of approximately 76 N/cm (1.7 lb/mm.) The calcined extrudate material was generally comprised of amorphous phase $ZrO_2$ as indicated by the XRD data.

Example 7

Tungsten Promoter

A first solution (Solution 1) was prepared by dissolving 25 g of $H_2WO_4$ (tungstic acid) in a mixed solution of 200 mL of 30% ammonia hydroxide and 200 mL of DI-$H_2O$. 250 g of zirconyl nitrate solution (20% $ZrO_2$) was prepared (Solution 2). Both Solution 1 and Solution 2 were preheated to approximately 30° C. Then, Solution 2 was added to Solution 1 drop-wise which facilitated precipitation of a zirconyl salt. The precipitate was aged in the mother liquor for approximately one hour at approximately 30° C. Thereafter, the precipitate was processed in a manner consistent with the processing procedure stated in Example 5 above.

The obtained extrudates had a surface area of approximately 40.6 $m^2/g$, a pore volume of approximately 0.168 cc/g and a crush strength value of approximately 125 N/cm (2.81 lb/mm.) The calcined extrudates were generally comprised of amorphous phase $ZrO_2$ as indicated by the XRD data.

Example 8

Molybdenum Promoter

An extrudate material of zirconium/molybdenum (Zr/Mo) may be prepared in a manner essentially consistent with the preparation and procedures provided in Example 4. The starting material providing the Mo source may be $(NH_4)_2MoO_2 \cdot xH_2O$.

Example 9

Effect of Polyacid/Promoter Material Choice

In addition to the aforementioned examples, additional experiments were conducted consistent with the examples provided above, wherein one or more supports were prepared in which the initial molar ratio (target) was approximately 4:1 in relation to the zirconium base compared to the polyacid/promoter material. Table 1 provides data from such experiments and examples, wherein the prepared extrudate includes a zirconium/phosphorous support, a zirconium/tungsten support, and a zirconium/chromium support, respectively. The zirconium/chromium support and zirconium/tungsten support data indicates a useful support may be obtained as seen by relatively high crush strength and surface area values.

TABLE 1

| SUPPORT | Zr/P | Zr/W | Zr/Cr |
|---|---|---|---|
| Molar Ratio (Zr:promoter) | 4:1 | 4:1 | 4:1 |
| Crush Strength | 1.71 lb/mm | 3.85 lb/mm | 3.79 lb/mm |
| Surface Area | 20.9 $m^2/g$ | 28.9 $m^2/g$ | 36.9 $m^2/g$ |
| Pore Volume | 0.191 cc/g | 0.155 cc/g | 0.197 cc/g |
| Crystalline Structure | Amorphous | Amorphous | Tetragonal |

Example 10

Chromium (VI) Promoter—8:1 Initial Molar Ratio

The following preparation and procedure serves as one representative and non-exhaustive model of a Zr/Cr extrudate material, wherein the initial molar ratio is approximately 8:1. 6.4 L of DI—$H_2O$ and 4 L of ammonium hydroxide (28-30% $NH_3$) were combined in a 20 L precipitation tank equipped with a heating jacket and continuous mixing. The resulting solution was heated to 35° C. 160 g of chromium (VI) oxide ($CrO_3$) was dissolved in 80 mL of DI-$H_2O$. The chromium solution was then mixed with 8000 g of zirconyl nitrate solution (20% $ZrO_2$). The chromium/zirconyl solution was then heated to 35° C. and pumped into the tank at a rate between 50 mL and 60 mL per minute. During the precipitation of the zirconyl salt, the pH was controlled at a minimum pH value of 8.5 by adding ammonium hydroxide as needed. After finishing the pumping, the precipitate was aged in mother liquor for approximately one hour.

The precipitate was then filtered, and then divided into small portions, and left to dry at ambient conditions. The material was allowed to dry until the LOI was in a range of 60% to 68%. The precipitate was then mixed and extruded (through a ⅛" die that generated a ⅛" extrudate) by using a lab screw extruder. The extrudate was then dried overnight (12 hours) at 110° C. and then was calcined in a muffle furnace with a temperature program of ambient temperature ramp at 5° C. per minute to 110° C. and dwell for approximately 2 hours, then to 600° C. at 5° C. per minute and dwell for 3 hours.

Example 11

Variations of Molar Ratio

Variations of the initial molar ratio (target) may be achieved in a manner consistent with the preparation and procedures provided in Example 8 above. Table 2 represents the data generated from Example 9, as well as other examples at the different initial molar ratios of 4:1, 12:1 and 16:1, respectively.

TABLE 2

| SUPPORT | Zr/Cr | Zr/Cr | Zr/Cr | Zr/Cr |
|---|---|---|---|---|
| Molar Ratio (Zr:Promoter) | 4:1 | 8:1 | 12:1 | 16:1 |
| Crush Strength | 3.79 lb/mm | 1.5 lb/mm | 2.1 lb/mm | 0.79 lb/mm |
| Surface Area | 36.9 m²/g | 30-38 m²/g | 35.3 m²/g | 33.9 m²/g |
| Pore Volume | 0.197 cc/g | 0.202 cc/g | 0.192 cc/g | 0.227 cc/g |

Example 12

Comparative Example—No Polyacid/Promoter Material

A 100 g solution of zirconyl nitrate (20% $ZrO_2$) was prepared and added drop-wise into a 200 mL solution of diluted $NH_3H_2O$ (15%). The mixing of the solutions yielded a change in pH from a value of approximately 12 to approximately 10. The pH value change facilitated zirconium precipitation. The precipitate was aged in the mother liquor for approximately 12 hours at ambient temperature. The final pH value was approximately 8.4. Thereafter, the precipitate was processed in a manner consistent with the processing procedure stated in Example 5 above. The obtained extrudate material possessed a crush strength value of approximately 22 N/cm (0.5 lb/mm.)

Based on the Examples provided above, it is envisioned that such a support/carrier may be used with one or more catalytically active metals for use in the conversion of glycerol or sugar alcohols into polyols or alcohols having fewer carbon and/or oxygen atoms, including, but not limited to, propylene glycol (1,2-propanediol), ethylene glycol (1,2-ethanediol), glycerin, trimethylene glycol (1,3-propanediol), methanol, ethanol, propanol, butanediols, and combinations thereof. Typical catalytically active elements for use in the conversion of glycerol and sugar alcohols include, but are not limited to, Group 4 (Group IVA), Group 10 (Group VIII) and Group 11 (Group IB) metals, such as copper, nickel, tin, ruthenium, rhenium, platinum, palladium, cobalt, iron and combinations thereof.

Example 13

Glycerin to Propylene Glycol—Cr Promoted Support/Cu Catalyst

A Zr/Cr support or carrier prepared in a manner consistent with the processes described above has been found particularly useful in the selective conversion of glycerin to propylene glycol. In one embodiment, the Zr/Cr support/carrier is dipped in or impregnated to achieve a copper (Cu) load in the range of approximately 5%-30%. The Cu—Zr/Cr catalyst cracks the carbon-oxygen bond in glycerin and enables conversion of glycerin to propylene glycol. As summarized in Table 3 below, one sample provides approximately 15% copper load and achieved a conversion of 72% and a selectivity for propylene glycol (PG) of 85 molar %. Another sample provides a 10% copper load, and yields a conversion of approximately 42% of the glycerin, and selectivity for propylene glycol of approximately 82 molar %.

TABLE 3

| Cu Load (%) | 15 | 10 |
|---|---|---|
| Conversion of Glycerin (%) | 72 | 42 |
| Selectivity for PG (molar %) | 85 | 82 |

Example 14

Sorbitol to Propylene Glycol—Cr Promoted Support/Ni—Sn Catalyst

A Zr/Cr support or carrier prepared in a manner consistent with the processes described above has been found particularly useful in the selective conversion of sorbitol to propylene glycol, ethylene glycol and glycerin. In one embodiment, the Zr/Cr support or carrier is co-dipped in or co-impregnated to achieve a nickel (Ni) load in the range of 10% to 30% and a tin (Sn) promoter in the range of 300-5000 parts per million (ppm). The nickel catalyst/tin promoter, on the Zr/Cr support, crack both the carbon-carbon and the carbon-oxygen bonds in sorbitol and enables conversion of sorbitol to a mix of propylene glycol, ethylene glycol and glycerin, as well as other minor compounds such as methanol, ethanol, propanol and butanediols. As summarized in Table 4 below, one sample provides a target load value of 10% nickel and 300 ppm tin. The tests were run in a fixed bed reactor. After loading, the catalysts were reduced under 100% $H_2$, 500° C. and ambient pressure at GSHV of 1000/hr for 8 hours. After reduction, a 25 wt. % sorbitol feed consisting of a molar ratio of Sorbitol/NaOH of 10:1 was pumped through the reactor under 120 bar and 210° C. under LSHV=1/hr, $H_2$/sorbitol molar ratio of 10:1. This load combination generates a conversion of 70.6% having selectivity for propylene glycol of 36.6 molar %, 14.7 molar % for ethylene glycol and 20.9 molar % for glycerin. In another sample, a target load value of 10% nickel and 700 ppm tin generates a conversion of 75.8% and selectivity for propylene glycol of 27.5 molar %, 12.4 molar % for ethylene glycol and 20.7 molar % for glycerin.

TABLE 4

| Ni Load (%) | | 10 | 10 |
|---|---|---|---|
| Sn Load (ppm) | | 300 | 700 |
| Conversion of Sorbitol (%) | | 70.6 | 75.8 |
| Selectivity (molar %) | PG | 36.6 | 27.5 |
| | EG | 14.7 | 12.4 |
| | Glycerin | 20.9 | 20.7 |

Example 15

Sorbitol to Propylene Glycol—Cr Promoted Support/Ni—Cu Catalyst

The extrudates prepared by co-precipitation of Zr and Cr(VI) (refer to Example 10 above) were loaded with 10% Ni and 1% Cu by incipient wetness. After calcinations, the catalyst was loaded to a tubular reactor and reduced under 100% $H_2$, 180° C. and ambient pressure at a Gaseous Space Hourly Velocity (GSHV) of 1000/hr for 15 hours. After reduction, a 25 wt. % sorbitol feed consisting of a molar ratio of Sorbitol/ NaOH of 10:1 was pumped through the reactor under 120 bar and 210° C. under a Liquid Space Hourly Velocity (LSHV)= 2/hr. The test was run for 350 hours under these conditions. An average of 71% sorbitol conversion was achieved. Selectivity for three major products, ethylene glycol, propylene glycol, and glycerin, were 13 molar %, 27.8 molar %, and 37.8 molar %, respectively.

It is to be understood that the embodiments and claims are not limited in application to the details of construction and arrangement of the components set forth in the description. Rather, the description provides examples of the embodiments envisioned, but the claims are not limited to any particular embodiment or a preferred embodiment disclosed and/or identified in the specification. The embodiments and claims disclosed herein are further capable of other embodiments and of being practiced and carried out in various ways, including various combinations and sub-combinations of the features described above but that may not have been explicitly disclosed in specific combinations and sub-combinations. Accordingly, those skilled in the art will appreciate that the conception upon which the embodiments and claims are based may be readily utilized as a basis for the design of other compositions, structures, methods, and systems. In addition, it is to be understood that the phraseology and terminology employed herein are for the purpose of description and should not be regarded as limiting the claims.

What is claimed is:

1. A process for converting a sugar or sugar alcohol having a carbon-chain backbone to a polyol and/or an alcohol, the polyol and/or alcohol having a shorter carbon-chain backbone than the sugar or sugar alcohol, the process comprising the steps of:
   selecting a catalyst comprising a support comprising zirconium oxide and a promoter selected from the group consisting of oxide and acid forms of chromium, molybdenum and tungsten, phosphoric acid, sulfuric acid and organic polyacids; and at least one catalytically active metal selected from the group consisting of copper, nickel, tin, ruthenium, rhenium, platinum, palladium, cobalt, iron and combinations thereof;
   introducing the catalyst to the sugar or sugar alcohol under reaction conditions;
   providing a source of hydrogen; and
   converting at least 40 wt. % of the sugar or sugar alcohol to the polyol and/or alcohol.

2. The process of claim 1, wherein the polyol and/or alcohol comprises at least one of propylene glycol (1,2-propanediol), ethylene glycol, trimethylene glycol (1,3-propanediol), glycerin, methanol, ethanol, propanol and butandiols.

3. The process of claim 1 wherein the promoter is selected from the group consisting of $CrO_3$, $Cr_2O_3$, and combinations thereof.

4. The process of claim 3, wherein a molar ratio of zirconium to chromium is in a range between 4:1 and 20:1.

5. The process of claim 1 wherein the catalytically active metal is selected from the group consisting of nickel, tin and combinations thereof.

6. The process of claim 1 wherein the catalytically active metal is copper.

7. The process of claim 1, wherein at least 50% of the sugar or sugar alcohol is converted to the polyol and/or alcohol.

8. A process for converting glycerin having a selectivity for propylene glycol at reaction conditions, the process comprising the steps of:
   selecting a catalyst comprising a support comprising zirconium oxide and a promoter selected from the group consisting of oxide and acid forms of chromium, molybdenum and tungsten, phosphoric acid, sulfuric acid and organic polyacids, and one or more catalytically active metals comprising copper;
   introducing the catalyst to the glycerin under reaction conditions;
   providing a source of hydrogen; and
   converting at least 40% of the glycerin to propylene glycol.

9. A process for converting sorbitol with a selectivity for propylene glycol, ethylene glycol and/or glycerin at reaction conditions, the process comprising the steps of:
   selecting a catalyst comprising a support comprising zirconium oxide and a promoter selected from the group consisting of oxide and acid forms of chromium, molybdenum and tungsten, phosphoric acid, sulfuric acid and organic polyacids, and one or more catalytically active metals comprising a combination of nickel and tin;
   introducing the catalyst to the sorbitol under reaction conditions;
   providing a source of hydrogen; and
   converting at least 65% of the sorbitol to a combination of propylene glycol, ethylene glycol and/or glycerin.

10. The process of claim 8 wherein the zirconium oxide and the promoter are present in the support in a molar ratio of about 4:1 to about 12:1.

11. The process of claim 8 wherein the zirconium oxide and the promoter are present in the support in a molar ratio of about 8:1 to about 12:1.

12. The process of claim 8 wherein a target load of copper on the support is in a range between 5 wt. % and 30 wt. %.

13. The process of claim 8 wherein a target load of copper on the support is in a range between 10 wt. % to 20 wt. %.

14. The process of claim 8 wherein a target load of copper on the support is about 10 wt. %, and the process achieves a conversion rate of glycerin to propylene glycol of at least 40% and a selectivity to propylene glycol of at least 75 molar %.

15. The process of claim 8 wherein a target load of copper on the support is about 15 wt. %, and the process achieves a conversion rate of glycerin to propylene glycol of at least 65% and a selectivity of propylene glycol of at least 85 molar %.

16. The process of claim 9 wherein a target load of nickel on the support is about 10 wt. % to 30 wt. % and a target load of tin on the support is about 200 ppm to 5000 ppm.

17. The process of claim 16 wherein the target load of tin on the support is about 300 ppm.

18. The process of claim 17 wherein the conversion rate of sorbitol is at least 65%, the selectivity for propylene glycol is in a range between 35 molar % and 45 molar %, the selectivity for ethylene glycol is in a range between 10 molar % and 20 molar %, and the selectivity for glycerin in a range between 15 molar % and 25 molar %.

19. The process of claim 18 wherein the load of tin on the support is approximately 700 ppm and the process achieves a conversion rate of sorbitol of at least 70% and a selectivity for propylene glycol in a range between 25 molar % and 35 molar %, a selectivity for ethylene glycol in a range between 10 molar and 20 molar %, and a selectivity for glycerin in a range between 15 molar % and 25 molar %.

20. The process of claim 1 wherein the catalytically active metal is copper, a combination of nickel and copper, or a combination of nickel and tin.

21. The process of claim 1, wherein the process is a process for converting glycerol.

22. The process of claim 1, wherein the promoter is phosphoric acid.

23. The process of claim 1, wherein the conversion is performed at a temperature from about 180° C. to about 250° C., and a partial pressure of hydrogen of 100 bar to 160 bar.

24. The process of claim 1, wherein
the promoter is selected from the group consisting of $CrO_3$, $Cr_2O_3$, and combinations thereof;
the molar ratio of zirconium to chromium is in a range between 4:1 to 20:1; and
the catalytically active metal is copper, a combination of nickel and copper, or a combination of nickel and tin.

25. The process of claim 24, wherein the conversion is performed at a temperature from about 180° C. to about 250° C., and a partial pressure of hydrogen of 100 bar to 160 bar.

26. The process of claim 8 wherein the promoter is selected from the group consisting of $CrO_3$, $Cr_2O_3$, and combinations thereof, and wherein the molar ratio of zirconium to chromium is in a range between 4:1 to 20:1.

27. The process of claim 9 wherein the promoter is selected from the group consisting of $CrO_3$, $Cr_2O_3$, and combinations thereof, and wherein the molar ratio of zirconium to chromium is in a range between 4:1 to 20:1.

* * * * *